(12) United States Patent
Kremer et al.

(10) Patent No.: US 12,084,401 B2
(45) Date of Patent: *Sep. 10, 2024

(54) TRISAMIDE COMPOUNDS AND COMPOSITIONS COMPRISING THE SAME

(71) Applicant: Milliken & Company, Spartanburg, SC (US)

(72) Inventors: Daniel Kremer, Bayreuth (DE); Hans-Werner Schmidt, Bayreuth (DE); Paul Smith, Klosters (CH); John David Anderson, Woodruff, SC (US); Suchitra Datta, Spartanburg, SC (US); Keith Keller, Spartanburg, SC (US); Nathan Mehl, Spartanburg, SC (US); Walter Scrivens, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/197,660

(22) Filed: May 15, 2023

(65) Prior Publication Data

US 2023/0312460 A1    Oct. 5, 2023

Related U.S. Application Data

(63) Continuation of application No. 17/121,711, filed on Dec. 14, 2020, now Pat. No. 11,667,603.

(60) Provisional application No. 62/947,476, filed on Dec. 12, 2019.

(51) Int. Cl.
C07C 237/42    (2006.01)
C08K 5/20      (2006.01)

(52) U.S. Cl.
CPC .............. *C07C 237/42* (2013.01); *C08K 5/20* (2013.01)

(58) Field of Classification Search
CPC .................................. C07C 237/42; C08K 5/20
See application file for complete search history.

(56) References Cited

U.S. PATENT DOCUMENTS

| | | | |
|---|---|---|---|
| 8,415,416 | B2 | 4/2013 | Chin |
| 10,316,168 | B2 | 6/2019 | Hill |
| 2007/0066687 | A1 | 3/2007 | Kitagawa |
| 2007/0142514 | A1 | 6/2007 | Ishikawa |
| 2007/0149663 | A1 | 6/2007 | Schmidt |
| 2007/0170398 | A1 | 7/2007 | Schmidt |
| 2008/0249269 | A1 | 10/2008 | Chin |
| 2010/0016491 | A1 | 1/2010 | Niga |
| 2011/0136950 | A1 | 6/2011 | Yu |
| 2015/0114257 | A1 | 4/2015 | Takagi |

FOREIGN PATENT DOCUMENTS

| | | |
|---|---|---|
| JP | 2010070621 A | 4/2010 |
| JP | 2013088612 | 5/2013 |
| TW | 585886 | 5/2004 |
| TW | 200420641 | 10/2004 |
| WO | 0246300 A2 | 6/2002 |
| WO | 2002046300 | 6/2002 |
| WO | 2003102069 | 12/2003 |
| WO | 2004072168 A2 | 8/2004 |
| WO | 2008122525 | 10/2008 |
| WO | 2010069854 A2 | 6/2010 |
| WO | 2017156099 | 9/2017 |
| WO | 2021119632 A1 | 6/2021 |
| WO | 2021119633 A1 | 6/2021 |

OTHER PUBLICATIONS

Abraham, F et al., "Synthesis and Structure-Efficiency Relations of 1,3,5-Benzenetrisamides as Nucleating Agents and Clarifiers for Isotactic Poly(propylene)," Macromol. Chem. Phys. 2010, 211, 171-181.
English machine translation of JP 2010-070621. (Year: 2010) 28 pages.
International Search Report and Written Opinion for App. No. PCT/US2020/064958, dated Mar. 19, 2021, 10 pages.
International Search Report and Written Opinion for App. No. PCT/US2020/064959, dated Apr. 7, 2021, 10 pages.
International Search Report and Written Opinion for App. No. PCT/US2021/061635, dated Mar. 14, 2022, 13 pages.

*Primary Examiner* — John E Uselding
(74) *Attorney, Agent, or Firm* — Robert M. Lanning

(57) ABSTRACT

A trisamide compound has the structure of Formula (I)

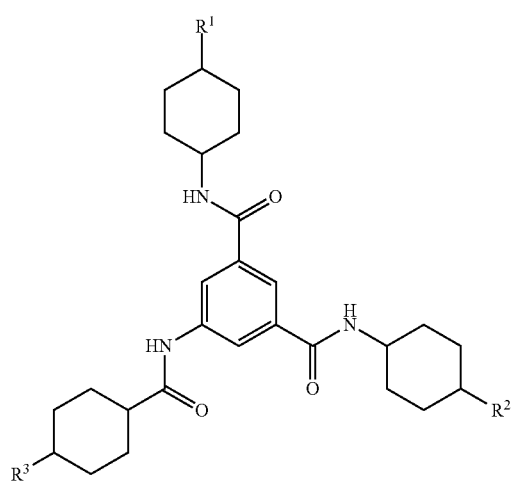

(I)

in which $R^1$, $R^2$, and $R^3$ are independently selected from the group consisting of alkyl groups. A polymer composition comprises a trisamide compound of Formula (I) and a polyolefin polymer. The polymer compositions containing a trisamide compound of Formula (I) exhibit very low haze levels and minimal extraction of the trisamide compound.

28 Claims, No Drawings

TRISAMIDE COMPOUNDS AND COMPOSITIONS COMPRISING THE SAME

CROSS-REFERENCE TO RELATED PATENT APPLICATIONS

This application is a continuation of U.S. patent application Ser. No. 17/121,711 filed on Dec. 14, 2020, which application claims, pursuant to 35 U.S.C. § 119(e), priority to and the benefit of the filing date of U.S. Patent Application No. 62/947,476 filed on Dec. 12, 2019, the contents of which are hereby incorporated by reference.

TECHNICAL FIELD OF THE INVENTION

This application relates to trisamide compounds (specifically, trisamide derivatives formally derived from 5-aminoisophthalic acid) and compositions comprising the same.

BACKGROUND OF THE INVENTION

Polymer resins are widely used in a variety of areas due to, among other things, their excellent processability, mechanical properties (especially on a relative weight basis), and electrical properties. Although the polymers themselves may have beneficial properties, additives may be used to further enhance those properties and/or mitigate shortcomings.

Polyolefins are a group of polymer resins that are particularly versatile. Polyolefins are semicrystalline polymers. A polyolefin which has been allowed to cool relatively slowly (e.g., such as the cooling that takes place during the production of molded plastic parts) contains amorphous regions in which the polymer chains are randomly arranged and crystalline regions in which the polymer chains have assumed an orderly configuration. Within these crystalline regions of the polyolefin, the polymer chains align into domains commonly referred to as "crystalline lamellae." Under normal processing conditions, the crystalline lamellae grow radially in all directions as the polyolefin polymer cools from the molten state. This radial growth results in the formation of spherulites, which are spherical semicrystalline regions composed of multiple crystalline lamellae interrupted by amorphous regions. The size of the spherulites is affected by several parameters and can range from hundreds of nanometers to millimeters in diameter. When the spherulite size is appreciably larger than the wavelength of visible light, the spherulites will scatter visible light passing through the polymer. This scattering of visible light results in a hazy appearance which is commonly referred to as "polymer haze" or simply "haze." While appreciable levels of polymer haze may be acceptable in some applications, there are certain applications (e.g., storage containers) in which consumers desire relatively transparent plastics, which requires correspondingly low haze levels.

Over the years, several approaches have been developed to reduce haze in polyolefins. One approach that has enjoyed much commercial success entails the use of clarifying agents. Clarifying agents are additives (frequently organic compounds) that, when melt processed with the polymer, nucleate the crystallization of the cooling polymer and reduce spherulite size or even substantially prevent the formation of these efficient light scattering entities. For example, bis(3,4-dimethylbenzylidene)sorbitol enjoyed much commercial success because of its ability to reduce haze in polypropylene polymers. However, bis(3,4-dimethylbenzylidene)sorbitol was not without its limitations. In particular, the clarifying agent is unable to reduce haze in polypropylene polymers to a point that rivals the haze levels of more transparent polymers, such as polystyrene and acrylic resins. The residual haze of polymers clarified with bis(3,4-dimethylbenzylidene)sorbitol limits their applications and end uses.

Other clarifying agents have been developed in an attempt to address the limitations of the sorbitol acetals (e.g., bis(3,4-dimethylbenzylidene)sorbitol). For example, trisamide compounds (e.g., trisamide derivatives formally derived from 1,3,5-benzenetriamine, 3,5-diaminobenzoic acid, 5-aminoisophthalic acid, or trimesic acid) initially showed promise due to the fact that relatively low loadings of such compounds could produce haze levels in polypropylene polymers that rivaled those achieved with bis(3,4-dimethylbenzylidene)sorbitol. Despite their initial promise, the disclosed trisamide compounds still cannot produce haze levels to rival those of the more transparent polymers. Furthermore, many of the disclosed trisamide compounds can be extracted from the polypropylene to which they are added. These undesirable levels of extraction render such trisamide compounds less suitable for use in food contact and medical applications (i.e., applications in which the polymer clarified with the trisamide compound comes into contact with food [e.g., food storage or packaging] or is used in medical devices [e.g., syringes]), where industry preference and/or regulatory requirements demand additives that exhibit minimal extraction from the polymer.

Thus, a need remains for clarifying agents that can both produce desirably low haze levels in polyolefin polymers and exhibit minimal extraction from the polyolefin polymer to which they are added. A need also remains for polymer compositions incorporating such clarifying agents and which exhibit the desired combination of low haze and minimal extraction of the clarifying agent. The various embodiments described herein seek to provide such clarifying agents and compositions.

BRIEF SUMMARY OF THE INVENTION

In a first embodiment, the invention provides a compound of Formula (I)

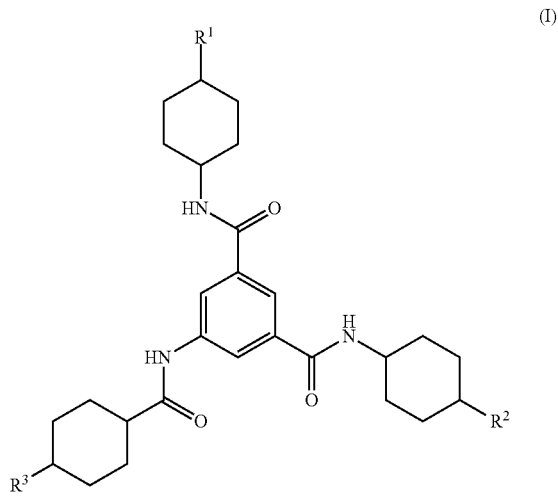

wherein $R^1$, $R^2$, and $R^3$ are independently selected from the group consisting of alkyl groups.

In a second embodiment, the invention provides a polymer composition comprising a compound of Formula (I) and a polyolefin polymer.

DETAILED DESCRIPTION OF THE INVENTION

In a first embodiment, the invention provides a compound of Formula (I) below, which is a trisamide derivative formally derived from 5-aminoisophthalic acid. The structure of Formula (I) is as follows:

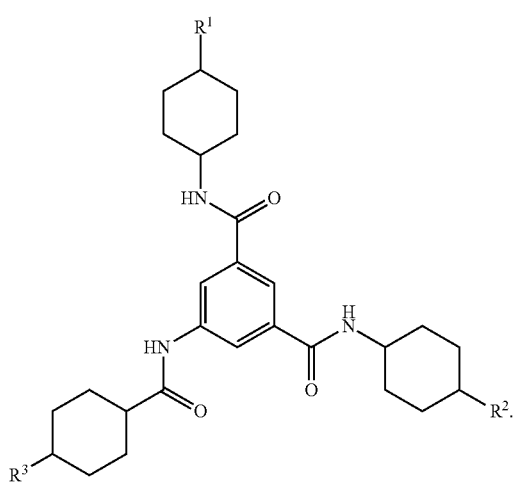

In Formula (I), the groups $R^1$, $R^2$, and $R^3$ are independently selected from the group consisting of alkyl groups.

The groups $R^1$, $R^2$, and $R^3$ can be any suitable alkyl group. In a preferred embodiment, $R^1$, $R^2$, and $R^3$ are independently selected from the group consisting of $C_1$-$C_{20}$ alkyl groups (e.g., $C_3$-$C_{20}$ alkyl groups), more preferably $C_1$-$C_{12}$ alkyl groups (e.g., $C_3$-$C_{12}$ alkyl groups), even more preferably $C_1$-$C_8$ alkyl groups (e.g., $C_3$-$C_8$ alkyl groups), and most preferably $C_1$-$C_5$ alkyl groups (e.g., $C_2$-$C_5$ alkyl groups or $C_3$-$C_5$ alkyl groups). Suitable alkyl groups can be either linear or branched. In a preferred embodiment, at least one of $R^1$, $R^2$, and $R^3$ is a branched alkyl group. If only one of $R^1$, $R^2$, and $R^3$ is a branched alkyl group, $R^3$ preferably is the branched alkyl group. In another embodiment when only one of $R^1$, $R^2$, and $R^3$ is a branched alkyl group, $R^1$ preferably is the branched alkyl group. In another preferred embodiment, at least two of $R^1$, $R^2$, and $R^3$ are independently selected branched alkyl groups. In one such embodiment, $R^1$ and $R^2$ preferably are independently selected branched alkyl groups. In another such embodiment, $R^2$ and $R^3$ preferably are independently selected branched alkyl groups. In yet another preferred embodiment, each of $R^1$, $R^2$, and $R^3$ is an independently selected branched alkyl group. In those embodiments containing branched alkyl groups, the alkyl group can contain any suitable number of carbon atoms, with preferred examples being $C_3$-$C_{20}$ branched alkyl groups, $C_3$-$C_{12}$ branched alkyl groups, $C_3$-$C_8$ branched alkyl groups, and $C_3$-$C_5$ branched alkyl groups. Suitable branched alkyl groups preferably contain a branch point located at the alpha-carbon or beta-carbon relative to the cyclohexanediyl moiety.

In a preferred embodiment, $R^1$, $R^2$, and $R^3$ are independently selected from the group consisting of n-propyl, isopropyl, n-butyl, sec-butyl (i.e., butan-2-yl or 1-methylpropyl), isobutyl (i.e., 2-methylpropyl), tert-butyl (i.e., 1,1-dimethylethyl), n-pentyl, tert-pentyl (i.e., 2-methylbutan-2-yl or 1,1-dimethylpropyl), neopentyl (i.e., 2,2-dimethylpropyl), isopentyl (i.e., 3-methylbutyl), se-pentyl (i.e., pentan-2-yl or 1-methylbutyl), sec-isopentyl (i.e., 3-methylbutan-2-yl or 1,2-dimethylpropyl), pentan-3-yl (i.e., 1-ethylpropyl), and 2-methylbutyl. In a more preferred embodiment, $R^1$, $R^2$, and $R^3$ are independently selected from the group consisting of n-propyl, isopropyl, n-butyl, sec-butyl (i.e., butan-2-yl or 1-methylpropyl), isobutyl (i.e., 2-methylpropyl), tert-butyl (i.e., 1,1-dimethylethyl), tert-pentyl (i.e., 2-methylbutan-2-yl or 1,1-dimethylpropyl), sec-pentyl (i.e., pentan-2-yl or 1-methylbutyl), sec-isopentyl (i.e., 3-methylbutan-2-yl or 1,2-dimethylpropyl), and pentan-3-yl (i.e., 1-ethylpropyl). In yet another preferred embodiment, $R^1$, $R^2$, and $R^3$ are independently selected from the group consisting of n-propyl, isopropyl, n-butyl, isobutyl (i.e., 2-methylpropyl), tert-butyl (i.e., 1,1-dimethylethyl), and tert-pentyl (i.e., 2-methylbutan-2-yl or 1,1-dimethylpropyl).

As noted above, at least one of $R^1$, $R^2$, and $R^3$ preferably is a branched alkyl group. Thus, in a preferred embodiment, at least one of $R^1$, $R^2$, and $R^3$ is selected from the group consisting of isopropyl, sec-butyl (i.e., butan-2-yl or 1-methylpropyl), isobutyl (i.e., 2-methylpropyl), tert-butyl (i.e., 1,1-dimethylethyl), tert-pentyl (i.e., 2-methylbutan-2-yl or 1,1-dimethylpropyl), neopentyl (i.e., 2,2-dimethylpropyl), isopentyl (i.e., 3-methylbutyl), se-pentyl (i.e., pentan-2-yl or 1-methylbutyl), sec-isopentyl (i.e., 3-methylbutan-2-yl or 1,2-dimethylpropyl), pentan-3-yl (i.e., 1-ethylpropyl), and 2-methylbutyl. In another preferred embodiment, at least one of $R^1$, $R^2$, and $R^3$ is selected from the group consisting of isopropyl, sec-butyl (i.e., butan-2-yl or 1-methylpropyl), isobutyl (i.e., 2-methylpropyl), tert-butyl (i.e., 1,1-dimethylethyl), tert-pentyl (i.e., 2-methylbutan-2-yl or 1,1-dimethylpropyl), se-pentyl (i.e., pentan-2-yl or 1-methylbutyl), sec-isopentyl (i.e., 3-methylbutan-2-yl or 1,2-dimethylpropyl), and pentan-3-yl (i.e., 1-ethylpropyl). In a more preferred embodiment, at least one of $R^1$, $R^2$, and $R^3$ is selected from the group consisting of isopropyl, isobutyl (i.e., 2-methylpropyl), tert-butyl (i.e., 1,1-dimethylethyl), and tert-pentyl (i.e., 2-methylbutan-2-yl or 1,1-dimethylpropyl). In yet another preferred embodiment, at least one of $R^1$, $R^2$, and $R^3$ is selected from the group consisting of tert-butyl (i.e., 1,1-dimethylethyl) and tert-pentyl (i.e., 2-methylbutan-2-yl or 1,1-dimethylpropyl). In a preferred embodiment, $R^3$ is a branched alkyl group selected from one of the groups set forth in this paragraph. In another preferred embodiment, $R^2$ and $R^3$ are each a branched alkyl group independently selected from one of the groups set forth in this paragraph. In yet another preferred embodiment, each of $R^1$, $R^2$, and $R^3$ is a branched alkyl group independently selected from one of the groups set forth in this paragraph.

In a preferred embodiment, the compound is selected from the group consisting of:

(i) N,N-di(4-isopropylcyclohexyl)-5-(4-n-propylcyclohexylcarbonylamino)isophthalamide;

(ii) N,N-di(4-isopropylcyclohexyl)-5-(4-isopropylcyclohexylcarbonylamino)isophthalamide;

(iii) N,N-di(4-isopropylcyclohexyl)-5-(4-n-butylcyclohexylcarbonylamino)isophthalamide;

(iv) N,N-di(4-isopropylcyclohexyl)-5-(4-tert-butylcyclohexylcarbonylamino)isophthalamide;

(v) N,N-di(4-isopropylcyclohexyl)-5-(4-n-pentylcyclohexylcarbonylamino)isophthalamide;

(vi) N,N-di(4-isopropylcyclohexyl)-5-(4-tert-pentylcyclohexylcarbonylamino)isophthalamide;

(vii) N,N-di(4-n-butylcyclohexyl)-5-(4-n-butylcyclohexylcarbonylamino)isophthalamide;
(viii) N,N-di(4-n-butylcyclohexyl)-5-(4-tert-butylcyclohexylcarbonylamino)isophthalamide;
(ix) N,N-di(4-sec-butylcyclohexyl)-5-(4-sec-butylcyclohexylcarbonylamino)isophthalamide;
(x) N,N-di(4-sec-butylcyclohexyl)-5-(4-tert-butylcyclohexylcarbonylamino)isophthalamide;
(xi) N,N-di(4-tert-butylcyclohexyl)-5-(4-n-propylcyclohexylcarbonylamino)isophthalamide;
(xii) N,N-di(4-tert-butylcyclohexyl)-5-(4-isopropylcyclohexylcarbonylamino)isophthalamide;
(xiii) N,N-di(4-tert-butylcyclohexyl)-5-(4-n-butylcyclohexylcarbonylamino)isophthalamide;
(xiv) N,N-di(4-tert-butylcyclohexyl)-5-(4-tert-butylcyclohexylcarbonylamino)isophthalamide
(xv) N,N-di(4-tert-butylcyclohexyl)-5-(4-n-pentylcyclohexylcarbonylamino)isophthalamide;
(xvi) N,N-di(4-tert-pentylcyclohexyl)-5-(4-tert-butylcyclohexylcarbonylamino)isophthalamide;
(xvii) N,N-di(4-tert-pentylcyclohexyl)-5-(4-tert-pentylcyclohexylcarbonylamino)isophthalamide; and
(xviii) mixtures thereof (i.e., mixtures of two or more of any of the foregoing compounds).

In another preferred embodiment, the compound is selected from the group consisting of:
(i) N,N-di(4-isopropylcyclohexyl)-5-(4-tert-butylcyclohexylcarbonylamino)isophthalamide;
(ii) N,N-di(4-isopropylcyclohexyl)-5-(4-tert-pentylcyclohexylcarbonylamino)isophthalamide;
(iii) N,N-di(4-n-butylcyclohexyl)-5-(4-tert-butylcyclohexylcarbonylamino)isophthalamide;
(iv) N,N-di(4-sec-butylcyclohexyl)-5-(4-sec-butylcyclohexylcarbonylamino)isophthalamide;
(v) N,N-di(4-sec-butylcyclohexyl)-5-(4-tert-butylcyclohexylcarbonylamino)isophthalamide;
(vi) N,N-di(4-tert-butylcyclohexyl)-5-(4-n-propylcyclohexylcarbonylamino)isophthalamide;
(vii) N,N-di(4-tert-butylcyclohexyl)-5-(4-isopropylcyclohexylcarbonylamino)isophthalamide;
(viii) N,N-di(4-tert-butylcyclohexyl)-5-(4-tert-butylcyclohexylcarbonylamino)isophthalamide;
(ix) N,N-di(4-tert-pentylcyclohexyl)-5-(4-tert-butylcyclohexylcarbonylamino)isophthalamide;
(x) N,N-di(4-tert-pentylcyclohexyl)-5-(4-tert-pentylcyclohexylcarbonylamino)isophthalamide; and
(xi) mixtures thereof (i.e., mixtures of two or more of any of the foregoing compounds).

In one preferred embodiment, the compound of Formula (I) is N,N-di(4-tert-butylcyclohexyl)-5-(4-tert-butylcyclohexylcarbonylamino)isophthalamide. In another preferred embodiment, the compound of Formula (I) is N,N-di(4-tert-butylcyclohexyl)-5-(4-isopropylcyclohexylcarbonylamino)isophthalamide. In yet another preferred embodiment, the compound of Formula (I) is N,N-di(4-tert-butylcyclohexyl)-5-(4-n-butylcyclohexylcarbonylamino)isophthalamide. In another preferred embodiment, the compound of Formula (I) is N,N-di(4-tert-pentylcyclohexyl)-5-(4-tert-butylcyclohexylcarbonylamino)isophthalamide. In yet another preferred embodiment, the compound of Formula (I) is N,N-di(4-tert-butylcyclohexyl)-5-(4-n-propylcyclohexylcarbonylamino)isophthalamide. In another preferred embodiment, the compound of Formula (I) is N,N-di(4-isopropylcyclohexyl)-5-(4-tert-butylcyclohexylcarbonylamino)isophthalamide. In yet another preferred embodiment, the compound of Formula (I) is N,N-di(4-tert-pentylcyclohexyl)-5-(4-tert-pentylcyclohexylcarbonylamino)isophthalamide. In another preferred embodiment, the compound of Formula (I) is N,N-di(4-isopropylcyclohexyl)-5-(4-n-butylcyclohexylcarbonylamino)isophthalamide. In yet another preferred embodiment, the compound of Formula (I) is N,N-di(4-isopropylcyclohexyl)-5-(4-n-pentylcyclohexylcarbonylamino)isophthalamide. In another preferred embodiment, the compound of Formula (I) is N,N-di(4-tert-butylcyclohexyl)-5-(4-n-pentylcyclohexylcarbonylamino)isophthalamide. In yet another preferred embodiment, the compound of Formula (I) is N,N-di(4-isopropylcyclohexyl)-5-(4-tert-pentylcyclohexylcarbonylamino)isophthalamide. In another preferred embodiment, the compound of Formula (I) is N,N-di(4-isopropylcyclohexyl)-5-(4-n-propylcyclohexylcarbonylamino)isophthalamide. In yet another preferred embodiment, the compound of Formula (I) is N,N-di(4-n-butylcyclohexyl)-5-(4-tert-butylcyclohexylcarbonylamino)isophthalamide. In another preferred embodiment, the compound of Formula (I) is N,N-di(4-n-butylcyclohexyl)-5-(4-n-butylcyclohexylcarbonylamino)isophthalamide. In yet another preferred embodiment, the compound of Formula (I) is N,N-di(4-sec-butylcyclohexyl)-5-(4-sec-butylcyclohexylcarbonylamino)isophthalamide. In another preferred embodiment, the compound of Formula (I) is N,N-di(4-sec-butylcyclohexyl)-5-(4-tert-butylcyclohexylcarbonylamino)isophthalamide.

As can be seen in Formula (I), each cyclohexanediyl moiety is substituted with non-hydrogen substituents (i.e., the $R^1$, $R^2$, or $R^3$ group and the amide substituted benzene moiety) in both the 1- and 4-positions. The non-hydrogen substituents attached to each cyclohexanediyl moiety can be arranged in two different spatial arrangements relative to each other. Both non-hydrogen substituents can lie on the same side of the mean plane of the cyclohexane ring, which corresponds to the cis-configuration, or both non-hydrogen substituents can lie on opposite sides of the mean plane of the cyclohexane ring, which corresponds to the trans-configuration. Each of the $R^1$, $R^2$, and $R^3$ groups can be disposed in either the cis-position or trans-position relative to the non-hydrogen substituent attached to the 1-position of the corresponding cyclohexanediyl moiety. In a preferred embodiment, at least one of the $R^1$, $R^2$, and $R^3$ groups is disposed in the cis-position relative to the non-hydrogen substituent attached to the 1-position of the corresponding cyclohexanediyl moiety. In another preferred embodiment, at least two of the $R^1$, $R^2$, and $R^3$ groups are disposed in the cis-position relative to the non-hydrogen substituent attached to the 1-position of the corresponding cyclohexanediyl moiety. In yet another preferred embodiment, each of the $R^1$, $R^2$, and $R^3$ groups is disposed in the cis-position relative to the non-hydrogen substituent attached to the 1-position of the corresponding cyclohexanediyl moiety.

In a preferred embodiment, the compound is selected from the group consisting of
(i) N,N-di(cis-4-isopropylcyclohexyl)-5-(cis-4-n-propylcyclohexylcarbonylamino)isophthalamide;
(ii) N,N-di(cis-4-isopropylcyclohexyl)-5-(cis-4-isopropylcyclohexylcarbonylamino)isophthalamide;
(iii) N,N-di(cis-4-isopropylcyclohexyl)-5-(cis-4-n-butylcyclohexylcarbonylamino)isophthalamide;
(iv) N,N-di(cis-4-isopropylcyclohexyl)-5-(cis-4-tert-butylcyclohexylcarbonylamino)isophthalamide;
(v) N,N-di(cis-4-isopropylcyclohexyl)-5-(cis-4-n-pentylcyclohexylcarbonylamino)isophthalamide;
(vi) N,N-di(cis-4-isopropylcyclohexyl)-5-(cis-4-tert-pentylcyclohexylcarbonylamino)isophthalamide;

(vii) N,N-di(cis-4-n-butylcyclohexyl)-5-(cis-4-n-butylcyclohexylcarbonylamino)isophthalamide;
(viii) N,N-di(cis-4-n-butylcyclohexyl)-5-(cis-4-tert-butylcyclohexylcarbonylamino)isophthalamide;
(ix) N,N-di(cis-4-sec-butylcyclohexyl)-5-(cis-4-sec-butylcyclohexylcarbonylamino)isophthalamide;
(x) N,N-di(cis-4-sec-butylcyclohexyl)-5-(cis-4-tert-butylcyclohexylcarbonylamino)isophthalamide;
(xi) N,N-di(cis-4-tert-butylcyclohexyl)-5-(cis-4-n-propylcyclohexylcarbonylamino)isophthalamide;
(xii) N,N-di(cis-4-tert-butylcyclohexyl)-5-(cis-4-isopropylcyclohexylcarbonylamino)isophthalamide;
(xiii) N,N-di(cis-4-tert-butylcyclohexyl)-5-(cis-4-n-butylcyclohexylcarbonylamino)isophthalamide;
(xiv) N,N-di(cis-4-tert-butylcyclohexyl)-5-(cis-4-tert-butylcyclohexylcarbonylamino)isophthalamide
(xv) N,N-di(cis-4-tert-butylcyclohexyl)-5-(cis-4-n-pentylcyclohexylcarbonylamino)isophthalamide;
(xvi) N,N-di(cis-4-tert-pentylcyclohexyl)-5-(cis-4-tert-butylcyclohexylcarbonylamino)isophthalamide;
(xvii) N,N-di(cis-4-tert-pentylcyclohexyl)-5-(cis-4-tert-pentylcyclohexylcarbonylamino)isophthalamide; and
(xviii) mixtures thereof (i.e., mixtures of two or more of any of the foregoing compounds).

In another preferred embodiment, the compound is selected from the group consisting of:
(i) N,N-di(cis-4-isopropylcyclohexyl)-5-(cis-4-tert-butylcyclohexylcarbonylamino)isophthalamide;
(ii) N,N-di(cis-4-isopropylcyclohexyl)-5-(cis-4-tert-pentylcyclohexylcarbonylamino)isophthalamide;
(iii) N,N-di(cis-4-n-butylcyclohexyl)-5-(cis-4-tert-butylcyclohexylcarbonylamino)isophthalamide;
(iv) N,N-di(cis-4-sec-butylcyclohexyl)-5-(cis-4-sec-butylcyclohexylcarbonylamino)isophthalamide;
(v) N,N-di(cis-4-sec-butylcyclohexyl)-5-(cis-4-tert-butylcyclohexylcarbonylamino)isophthalamide;
(vi) N,N-di(cis-4-tert-butylcyclohexyl)-5-(cis-4-n-propylcyclohexylcarbonylamino)isophthalamide;
(vii) N,N-di(cis-4-tert-butylcyclohexyl)-5-(cis-4-isopropylcyclohexylcarbonylamino)isophthalamide;
(viii) N,N-di(cis-4-tert-butylcyclohexyl)-5-(cis-4-tert-butylcyclohexylcarbonylamino)isophthalamide;
(ix) N,N-di(cis-4-tert-pentylcyclohexyl)-5-(cis-4-tert-butylcyclohexylcarbonylamino)isophthalamide;
(x) N,N-di(cis-4-tert-pentylcyclohexyl)-5-(cis-4-tert-pentylcyclohexylcarbonylamino)isophthalamide; and
(xi) mixtures thereof (i.e., mixtures of two or more of any of the foregoing compounds).

In one preferred embodiment, the compound of Formula (I) is N,N-di(cis-4-tert-butylcyclohexyl)-5-(cis-4-tert-butylcyclohexylcarbonylamino)isophthalamide. In another preferred embodiment, the compound of Formula (I) is N,N-di(cis-4-tert-butylcyclohexyl)-5-(cis-4-isopropylcyclohexylcarbonylamino)isophthalamide. In yet another preferred embodiment, the compound of Formula (I) is N,N-di(cis-4-tert-butylcyclohexyl)-5-(cis-4-n-butylcyclohexylcarbonylamino)isophthalamide. In another preferred embodiment, the compound of Formula (I) is N,N-di(cis-4-tert-pentylcyclohexyl)-5-(cis-4-tert-butylcyclohexylcarbonylamino)isophthalamide. In yet another preferred embodiment, the compound of Formula (I) is N,N-di(cis-4-tert-butylcyclohexyl)-5-(cis-4-n-propylcyclohexylcarbonylamino)isophthalamide. In another preferred embodiment, the compound of Formula (I) is N,N-di(cis-4-isopropylcyclohexyl)-5-(cis-4-tert-butylcyclohexylcarbonylamino)isophthalamide. In yet another preferred embodiment, the compound of Formula (I) is N,N-di(cis-4-tert-pentylcyclohexyl)-5-(cis-4-tert-pentylcyclohexylcarbonylamino)isophthalamide. In another preferred embodiment, the compound of Formula (I) is N,N-di(cis-4-isopropylcyclohexyl)-5-(cis-4-n-butylcyclohexylcarbonylamino)isophthalamide. In yet another preferred embodiment, the compound of Formula (I) is N,N-di(cis-4-isopropylcyclohexyl)-5-(cis-4-n-pentylcyclohexylcarbonylamino)isophthalamide. In another preferred embodiment, the compound of Formula (I) is N,N-di(cis-4-tert-butylcyclohexyl)-5-(cis-4-n-pentylcyclohexylcarbonylamino)isophthalamide. In yet another preferred embodiment, the compound of Formula (I) is N,N-di(cis-4-isopropylcyclohexyl)-5-(cis-4-tert-pentylcyclohexylcarbonylamino)isophthalamide. In another preferred embodiment, the compound of Formula (I) is N,N-di(cis-4-isopropylcyclohexyl)-5-(cis-4-n-propylcyclohexylcarbonylamino)isophthalamide. In yet another preferred embodiment, the compound of Formula (I) is N,N-di(cis-4-n-butylcyclohexyl)-5-(cis-4-tert-butylcyclohexylcarbonylamino)isophthalamide. In another preferred embodiment, the compound of Formula (I) is N,N-di(cis-4-n-butylcyclohexyl)-5-(cis-4-n-butylcyclohexylcarbonylamino)isophthalamide. In yet another preferred embodiment, the compound of Formula (I) is N,N-di(cis-4-sec-butylcyclohexyl)-5-(cis-4-sec-butylcyclohexylcarbonylamino)isophthalamide. In another preferred embodiment, the compound of Formula (I) is N,N-di(cis-4-sec-butylcyclohexyl)-5-(cis-4-tert-butylcyclohexylcarbonylamino)isophthalamide.

The present application also encompasses compositions containing one or more compounds of Formula (I), such as a composition containing a mixture of two or more compounds of Formula (I). (In this context, cis- and trans-isomers are considered different compounds such that a mixture of two or more isomers constitutes a composition containing a mixture of two or more compounds of Formula (I).) In such embodiments, it is preferred that 60% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. More preferably, about 65% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. In another preferred embodiment, about 70% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. In yet another preferred embodiment, about 75% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. In another preferred embodiment, about 80% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. In yet another preferred embodiment, about 85% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. In another preferred embodiment, about 90% or more of the $R^1$, $R^2$, and $R^3$ groups of all the compounds of Formula (I) present in the composition are in the cis-position relative to the non-hydrogen substituent attached to the 1-position of the corresponding cyclohexanediyl moiety. In yet another preferred embodiment, about 95% or more (e.g., about 96% or more, about 97% or more, about 98% or more, or about 99% or more) of the $R^1$, $R^2$, and $R^3$ groups of all the compounds of Formula (I) present in the composition are in the cis-position relative to the non-hydrogen substituent attached to the 1-position of the corresponding cyclohexanediyl moiety.

In another preferred embodiment of a composition containing a mixture of two or more compounds of Formula (I), about 60 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. More preferably, about 65 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. In yet another preferred embodiment, about 70 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. In another preferred embodiment, about 75 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. In yet another preferred embodiment, about 80 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. In another preferred embodiment, about 85 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. In yet another preferred embodiment, about 90 mol. % or more of the compounds of Formula (I) present in the composition have $R^1$, $R^2$, and $R^3$ groups that are each in the cis-position relative to the non-hydrogen substituent attached to the 1-position of the corresponding cyclohexanediyl moiety. In another preferred embodiment, about 95 mol. % or more (e.g., about 96 mol. % or more, about 97 mol % or more, about 98 mol. % or more, or about 99 mol. % or more) of the compounds of Formula (I) present in the composition have $R^1$, $R^2$, and $R^3$ groups that are each in the cis-position relative to the non-hydrogen substituent attached to the 1-position of the corresponding cyclohexanediyl moiety.

The compounds of Formula (I) can be produced using any suitable method or synthetic process. For example, the compound can be produced by first reacting the desired 4-alkylcyclohexylamine with 5-nitroisophthaloyl dichloride to produce an intermediate compound of Formula (A) below

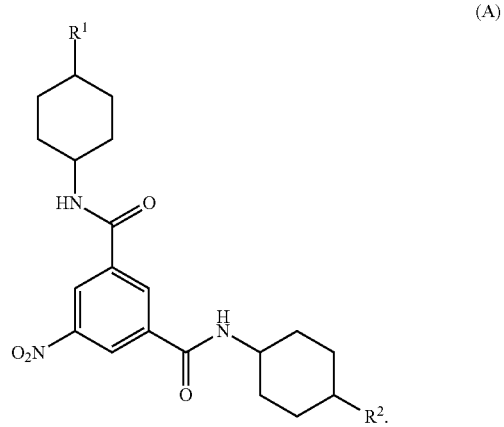

The intermediate compound of Formula (A) can then be hydrogenated using known methods to produce the corresponding amine compound of Formula (B) below

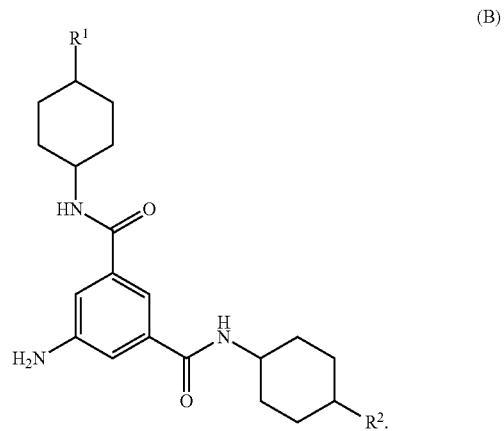

The amine compound of Formula (B) can then be reacted with the desired 4-alkylcyclohexanecarbonyl chloride to produce the desired compound of Formula (I).

Compounds of Formula (I) in which $R^1$ and $R^2$ are different can be produced, for example, by reacting a 5-nitroisophthalic acid monoalkyl ester (e.g., 5-nitroisophthalic acid monomethyl ester) with oxalyl chloride to produce an acid chloride compound of Formula (J) below

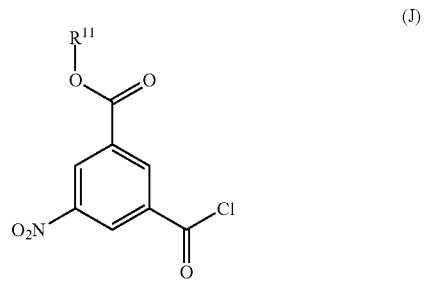

where $R^{11}$ is an alkyl group, such as a methyl group. The acid chloride compound of Formula (J) can then be reacted with the desired 4-alkylcyclohexylamine to produce the intermediate compound of Formula (K) below

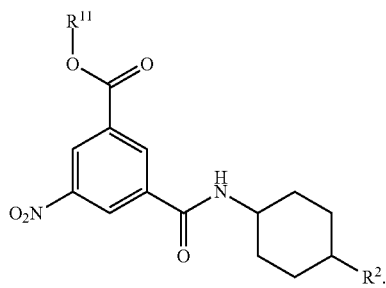

(K)

The intermediate compound of Formula (K) can then be saponified with an appropriate base (e.g., lithium hydroxide) to yield the corresponding carboxylate salt (e.g., lithium salt of the carboxylic acid) and alcohol (i.e., an alcohol having the structure $R^{11}OH$, such a methanol when $R^{11}$ is methyl). The corresponding carboxylate salt can then by hydrolyzed with an appropriate acid (e.g., hydrochloric acid) to produce the acid of Formula (L) below

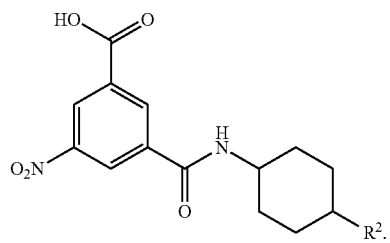

(L)

The acid of Formula (L) can then be reacted with oxalyl chloride to yield the corresponding acid chloride compound of Formula (M) below

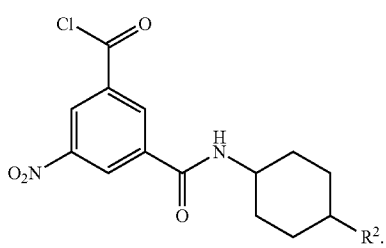

(M)

The acid chloride of Formula (M) can then be reacted with the desired 4-alkylcyclohexylamine to produce the intermediate compound of Formula (N) below

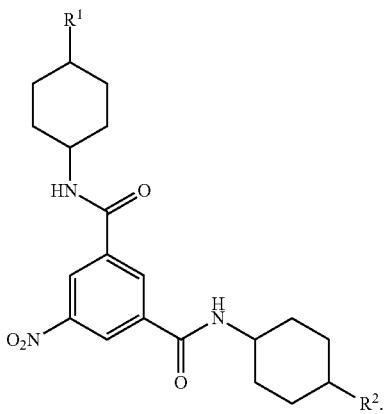

(N)

The intermediate compound of Formula (N) can then be reduced using known methods (e.g., hydrogenation) to produce the corresponding diamine compound of Formula (O) below

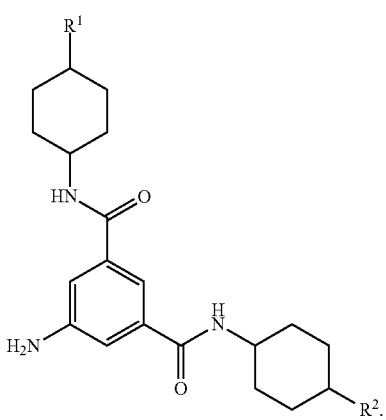

(O)

Finally, the intermediate compound of Formula (O) can be reacted with the desired 4-alkylcyclohexanecarbonyl chloride to yield the desired compound of Formula (I).

In a second embodiment, the invention provides a polymer composition comprising a compound of Formula (I) and a polymer. In such embodiment, the compound of Formula (I) can be any of the embodiments (e.g., specific compounds or compositions containing mixtures of compounds) discussed above in connection with the first embodiment of the invention.

The polymer composition can comprise any suitable polymer. Preferably, the polymer is a thermoplastic polymer, such as a polyolefin, polyester, polyamide, polylactic acid, polycarbonate, acrylic polymer, or mixture thereof. More preferably, the polymer is a polyolefin polymer, such as a polypropylene polymer, a polyethylene polymer, a polymethylpentene polymer (e.g., poly(4-methyl-1-pentene)), a polybutylene polymer, a poly(vinyl cyclohexane) polymer, and mixtures thereof. In a preferred embodiment, the polymer is a polypropylene polymer. More preferably, the polymer is selected from the group consisting of polypropylene homopolymers (e.g., atactic polypropylene homopolymer, isotactic polypropylene homopolymer, and syndiotactic polypropylene homopolymer), polypropylene copolymers (e.g., polypropylene random copolymers), polypropylene impact copolymers, and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylene-diene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %. In a preferred embodiment, the polymer composition comprises a polyolefin polymer selected from the group consisting of polypropylene homopolymers, polypropylene random copolymers, and mixtures thereof. More preferably, the polymer composition comprises a polypropylene random copolymer.

The polymer composition of the invention can contain any suitable amount of the compound(s) of Formula (I) described above. In a preferred embodiment, the polymer composition comprises, relative to the total weight of the composition, at least 0.001 wt. % of a compound of Formula (I). In another preferred embodiment, the polymer composition comprises, relative to the total weight of the composition, at least 0.002 wt. %, at least 0.003 wt. %, at least 0.004 wt. %, at least 0.005 wt. %, at least 0.01 wt. %, at least 0.02 wt. %, at least 0.03 wt. %, at least 0.04 wt. %, at least 0.05 wt. %, at least 0.1 wt. %, at least 0.3 wt. %, at least 0.5 wt. %, at least 1 wt. %, at least 5 wt. %, or at least 10 wt. % of a compound of Formula (I). In another embodiment, the polymer composition preferably comprises, relative to the total weight of the composition, less than 99 wt. % of a compound of Formula (I). In another preferred embodiment, the polymer composition comprises, relative to the total weight of the composition, less than 95 wt. %, less than 80 wt. %, less than 50 wt. %, less than 25 wt. %, less than 10 wt. %, less than 5 wt. %, less than 2 wt. %, less than 1 wt. %, less than 0.5 wt. %, less than 0.2 wt. %, less than 0.1 wt. %, or less than 0.07 wt. % of a compound of Formula (I). In a series of particularly preferred embodiments, the polymer composition comprises, relative to the total weight of the composition, 0.001 wt. % to 0.5 wt. % (e.g., 0.01 wt. % to 0.5 wt. % or 0.05 wt. % to 0.5 wt. %), 0.001 wt. % to 0.2 wt. % (e.g., 0.01 wt. % to 0.2 wt. % or 0.05 wt. % to 0.2 wt. %), 0.001 wt. % to 0.1 wt. % (e.g., 0.01 wt. % to 0.1 wt. % or 0.05 wt. % to 0.1 wt. %), or 0.001 wt. % to 0.07 wt. % (e.g., 0.01 wt. % to 0.07 wt. %) of a compound of Formula (I). As noted above, the polymer composition of the invention can comprise more than one compound of Formula (I). In those embodiments in which the polymer composition comprises more than one trisamide compound of Formula (I), each trisamide compound can be present in an amount falling within one of the ranges recited above, or the combined amount of all trisamide compounds can fall within one of the ranges recited above.

The polymer composition described herein can contain other polymer additives in addition to the compound(s) of Formula (I). Suitable additional polymer additives include, but are not limited to, antioxidants (e.g., phenolic antioxidants, phosphite antioxidants, and combinations thereof), anti-blocking agents (e.g., amorphous silica and diatomaceous earth), pigments (e.g., organic pigments and inorganic pigments) and other colorants (e.g., dyes and polymeric colorants), fillers and reinforcing agents (e.g., glass, glass fibers, talc, calcium carbonate, and magnesium oxysulfate whiskers), nucleating agents, clarifying agents, acid scavengers (e.g., metal salts of fatty acids, such as the metal salts of stearic acid), polymer processing additives (e.g., fluoropolymer polymer processing additives), polymer cross-linking agents, slip agents (e.g., fatty acid amide compounds derived from the reaction between a fatty acid and ammonia or an amine-containing compound), fatty acid ester compounds (e.g., fatty acid ester compounds derived from the reaction between a fatty acid and a hydroxyl-containing compound, such as glycerol, diglycerol, and combinations thereof), and combinations of the foregoing.

The polymer composition described herein can be produced by any suitable method. For example, the polyolefin composition can be produced by simple mixing (e.g., high shear or high intensity mixing) of the polyolefin polymer, the compound(s) of Formula (I), and any additional optional components. Alternatively, an additive composition comprising the compound(s) of Formula (I) and any additional optional components (such as those described above) can be pre-blended to provide a pre-blend composition. This pre-blend composition can then be mixed with the polymer to produce the polymer composition described above. The polymer composition can be provided in any form suitable for use in further processing to produce an article. For example, the polymer composition can be provided in the form of a powder (e.g., free-flowing powder), flake, pellet, prill, tablet, agglomerate, and the like.

The polymer composition described herein is believed to be useful in producing thermoplastic articles. The polymer composition can be formed into the desired thermoplastic article by any suitable technique, such as injection molding, injection rotational molding, blow molding (e.g., injection blow molding or injection stretch blow molding), extrusion (e.g., sheet extrusion, film extrusion, cast film extrusion, or foam extrusion), extrusion blow molding, thermoforming, rotomolding, film blowing (blown film), film casting (cast film), and the like.

The polymer composition described herein can be used to produce any suitable article or product. Suitable products include, but are not limited to, medical devices (e.g., pre-filled syringes for retort applications, intravenous supply containers, and blood collection apparatus), food packaging, liquid containers (e.g., containers for drinks, medications, personal care compositions, shampoos, and the like), apparel cases, microwavable articles, shelving, cabinet doors, mechanical parts, automobile parts, sheets, pipes, tubes, rotationally molded parts, blow molded parts, films, fibers, and the like.

The polymer composition of the invention has been observed to exhibit a very desirable combination of low haze coupled with low extraction of the trisamide compound of Formula (I). Polymer compositions (e.g., polypropylene random copolymer compositions) containing a compound of Formula (I) generally exhibit haze levels that are at least 15% lower than the haze levels exhibited by polymer compositions containing structurally similar trisamide compounds that are not encompassed by Formula (I). Further, polymer compositions containing certain compounds of Formula (I) have been observed to exhibit single digit haze levels that rival those exhibited by more transparent polymers, such as polystyrene and acrylic polymers. As noted above, these polymer compositions also exhibit exceptionally good (i.e., low) extraction of the compound of Formula (I) from the polymer composition. Indeed, polymer compositions containing certain compounds of Formula (I) have been observed to exhibit extraction levels that are one to two orders of magnitude less than the extraction levels exhibited by polymer compositions containing structurally similar trisamide compounds that are not encompassed by Formula (I). These properties exhibited by the inventive polymer compositions are believed to make the polymer compositions especially well-suited for use in making thermoplastic articles or products requiring low haze levels and low extraction, such as articles and products destined for food contact and medical applications.

The following examples further illustrate the subject matter described above but, of course, should not be construed as in any way limiting the scope thereof.

Example 1

This example demonstrates the synthesis of a trisamide compound of the invention (i.e., a trisamide compound of Formula (I)).

16.00 g (64.51 mmol) of 5-nitroisophthaloyl dichloride was added under inert atmosphere to 400 mL of dried tetrahydrofuran (THF). 12 mL of dry pyridine was also added, and the solution was cooled to 25° C. with the help of a water bath. Then 22.44 g (144.5 mmol) of cis-4-tert-butylcyclohexyl-amine was added to the solution followed by 200 mL of anhydrous THF. The solution was stirred for 23 hours at room temperature. Afterwards, THF was removed via rotary evaporation and 300 mL of methanol was added to the crude product. The methanol/product slurry was added to 2.5 L of stirred deionized (DI) water. The resulting mixture was stirred for 15 min and the solids collected by suction filtration. After rinsing the collected solids with 200 mL of DI water, the solids were then slurried with DI water (2×1500 mL×20 min) and collected by filtration. The crude product was then slurried in methanol (3×700 mL×60 min) and collected by suction filtration. The isolated solids were then dried in a vacuum oven at 85° C. for 23 hours. The reaction yielded 27.52 g (87.8%) of a fine white powder which was N,N-bis(cis-4-(tert-butyl)cyclohexyl)-5-nitroisophthalamide.

13.50 g (27.80 mmol) of the N,N-bis(cis-4-(tert-butyl) cyclohexyl)-5-nitroisophthalamide was hydrogenated in a THF/MeOH mixture (1000 mL/300 mL) with 0.96 g Pd/C (10 wt %). A 2 L Parr reactor was closed and purged 4 times with nitrogen and 5 times with hydrogen while stirring. The hydrogenation was carried out at 40° C. and a hydrogen pressure of 90 psig for 24 h. The reaction mixture was transferred under inert atmosphere into a flask and filtered through a Whatman binder-free glass microfiber filter (2.7 μm) to remove catalyst from the reaction material. The THF/MeOH solvent mixture was removed via rotary evaporation and the solids were slurried with diethyl ether (200 mL) for 1 h and collected by suction filtration. Additional solids were collected from the diethyl ether filtrate. The combined solids were dried in a vacuum oven at 65° C. for 8 h. The hydrogenation yielded 12.27 g (96.8%) of 5-amino-N,N-bis(cis-4-(tert-butyl)cyclohexyl)isophthalamide.

6.08 g (13.34 mmol) of the 5-amino-N,N-bis(cis-4-(tert-butyl)cyclohexyl)isophthalamide obtained above was added under inert atmosphere to 600 mL dry tetrahydrofuran (THF). 1.3 mL of dry pyridine was added, and the solution was cooled to 15° C. with the help of an ice-water bath. Then 2.98 g (14.7 mmol) of cis-4-tert-butylcyclohexanecarboxylic acid chloride was added. The reaction mixture was stirred at 15° C. for 0.5 hour and for 21 h at 21° C. Approximately 400 mL was removed via rotary evaporation, after which 150 mL of acetone was charged to the reaction slurry and stirred for 15 min. The reaction slurry was then added into a beaker containing 3000 mL of DI water with agitation. Upon complete addition of the slurry, the system was stirred for 10 min and the product collected by suction filtration. The solids were rinsed with 200 mL of DI water and re-slurried in 1600 mL of an 80/20 solution of DI water/MeOH for 15 min. The solids were then collected by suction filtration. The crude product was re-slurried in 300 mL of isopropyl alcohol for 1 h and collected by suction filtration. The product solids were dried in a vacuum oven at 95° C. for 17 h. The reaction yielded 7.54 g (90.8%) of N,N-di(cis-4-tert-butylcyclohexyl)-5-(cis-4-tert-butylcyclohexylcarbonylamino)isophthalamide.

Example 2

This example demonstrates the synthesis of a trisamide compound of the invention (i.e., a trisamide compound of Formula (I)).

13.50 g (54.45 mmol) of 5-nitroisophthaloyl dichloride was added under inert atmosphere to 500 mL of dried THF. 10.2 mL of dry pyridine was also added, and the solution was cooled to 25° C. with the help of a water bath. Then, 18.60 g (119.8 mmol) of cis-4-sec-butylcyclohexylamine was added to the solution followed by 200 mL of anhydrous THF. The solution was stirred for 23 hours at room temperature. Afterwards, THF was removed via rotary evaporation and 300 mL of IPA was added to the crude product. The IPA/product slurry was added to 2.8 L of stirred DI water. The resulting mixture was stirred for 20 min and the solids collected by suction filtration. After rinsing the collected solids with 1000 mL of DI water, the solids were then slurried in 250 mL of 5° C. IPA for 60 min and collected by filtration. The crude product was then rinsed with 100 mL of −78° C. diethyl ether. The isolated solids were then dried in a vacuum oven at 85° C. for 23 hours. The reaction yielded 22.57 g (85.4%) of a fine white powder which was N,N-bis (cis-4-(sec-butyl)cyclohexyl)-5-nitroisophthalamide.

22.57 g (46.47 mmol) of the N,N-bis(cis-4-(sec-butyl) cyclohexyl)-5-nitroisophthalamide) obtained above was hydrogenated in a THF/MeOH mixture (1000 mL/300 mL) with 1.60 g Pd/C (10 wt %). A 2 L Parr reactor was closed and purged 4 times with nitrogen and 5 times with hydrogen while stirring. The hydrogenation was carried out at 40° C. and a hydrogen pressure of 90 psig for 24 h. The reaction mixture was transferred under inert atmosphere into a flask and filtered through a Whatman binder-free glass microfiber filter (2.7 μm) to remove catalyst from the reaction material. The THF/MeOH solvent mixture was removed via rotary evaporation and the solids were slurried with IPA (200 mL) for 45 min and filtered. The collected solids were then rinsed with 75 mL of −78° C. diethyl ether. Additional solids were collected from the diethyl ether filtrate. The combined solids were dried in a vacuum oven at 45° C. for 18 h. The reaction yielded 19.45 g (91.8%) of 5-amino-N,N-bis(cis-4-(sec-butyl)cyclohexyl)isophthalamide.

9.64 g (21.16 mmol) of the 5-amino-N,N-bis(cis-4-(sec-butyl)cyclohexyl)isophthalamide obtained above was added under inert atmosphere to 900 mL dry Tetrahydrofuran (THF). 2.1 mL of dry pyridine was added and the solution was cooled to 15° C. with the help of an ice-water bath. Then 4.72 g (23.28 mmol) of cis-4-tert-butylcyclohexanecarboxylic acid chloride was added. The reaction mixture was stirred at 15° C. for 0.5 hour and for 21 h at 21° C. Approximately 600 mL was removed via rotary evaporation after which 150 mL of acetone was charged to the reaction slurry and stirred for 15 min. The reaction slurry was then added into a beaker containing 2500 mL of DI water with agitation. Upon complete addition of the slurry, the system was stirred for 10 min and the product collected by suction filtration. The solids were rinsed with 200 mL of DI water and re-slurried in 1200 mL of an 75/25 solution of DI water/IPA for 90 min. The solids were then collected by suction filtration. The crude product was re-slurried in 300 mL of 5° C. IPA for 30 min and collected by suction filtration. The product solids were dried in a vacuum oven at 110° C. for 17 h. The reaction yielded 12.65 g (96.1%) of N,N-di(cis-4-sec-butylcyclohexyl)-5-(cis-4-tert-butylcyclohexylcarbonylamino)isophthalamide.

Example 3

This example demonstrates the production of polymer compositions according to the invention and the properties of such polymer compositions.

Twenty trisamide compounds were first synthesized in accordance with the general procedure described above and demonstrated in Examples 1 and 2. The trisamide compounds are listed in Table 1 below. For the sake of simplicity in comparing the various compounds, the trisamide compounds all had similar cis-contents.

TABLE 1

Compound IDs and compound names for trisamide compounds used in making polymer compositions.

| Compound ID | Compound Name |
|---|---|
| Compound 1 | N,N-di(cyclohexyl)-5-(cyclohexylcarbonylamino)isophthalamide |
| Compound 2 | N,N-di(4-sec-butylcyclohexyl)-5-(4-sec-butylcyclohexylcarbonylamino)isophthalamide |
| Compound 3 | N,N-di(4-tert-butylcyclohexyl)-5-(4-n-butylcyclohexylcarbonylamino)isophthalamide |
| Compound 4 | N,N-di(4-sec-butylcyclohexyl)-5-(4-tert-butylcyclohexylcarbonylamino)isophthalamide |
| Compound 5 | N,N-di(4-tert-pentylcyclohexyl)-5-(4-tert-butylcyclohexylcarbonylamino)isophthalamide |
| Compound 6 | N,N-di(4-n-butylcyclohexyl)-5-(4-tert-butylcyclohexylcarbonylamino)isophthalamide |
| Compound 7 | N,N-di(4-tert-pentylcyclohexyl)-5-(4-tert-pentylcyclohexylcarbonylamino)isophthalamide |
| Compound 8 | N,N-di(4-isopropylcyclohexyl)-5-(4-tert-pentylcyclohexylcarbonylamino)isophthalamide |
| Compound 9 | N,N-di(4-tert-butylcyclohexyl)-5-(4-n-pentylcyclohexylcarbonylamino)isophthalamide |
| Compound 10 | N,N-di(4-isopropylcyclohexyl)-5-(4-tert-butylcyclohexylcarbonylamino)isophthalamide |
| Compound 11 | N,N-di(4-n-butylcyclohexyl)-5-(4-n-butylcyclohexylcarbonylamino)isophthalamide |
| Compound 12 | N,N-di(4-isopropylcyclohexyl)-5-(4-n-pentylcyclohexylcarbonylamino)isophthalamide |
| Compound 13 | N,N-di(4-tert-butylcyclohexyl)-5-(4-tert-butylcyclohexylcarbonylamino)isophthalamide |
| Compound 14 | N,N-di(4-tert-butylcyclohexyl)-5-(4-n-propylcyclohexylcarbonylamino)isophthalamide |
| Compound 15 | N,N-di(4-isopropylcyclohexyl)-5-(4-n-propylcyclohexylcarbonylamino)isophthalamide |
| Compound 16 | N,N-di(4-tert-butylcyclohexyl)-5-(4-isopropylcyclohexylcarbonylamino)isophthalamide |
| Compound 17 | N,N-di(4-isopropylcyclohexyl)-5-(4-n-butylcyclohexylcarbonylamino)isophthalamide |
| Compound 18 | N,N-di(4-methylcyclohexyl)-5-(4-methylcyclohexylcarbonylamino)isophthalamide |
| Compound 19 | N,N-di(cyclohexyl)-5-(4-isopropylcyclohexylcarbonylamino)isophthalamide |
| Compound 20 | N,N-di(cyclohexyl)-5-(4-tert-butylcyclohexylcarbonylamino)isophthalamide |

Polymer compositions were made by compounding each trisamide compound into a 12 MFR polypropylene random copolymer (SA849 RCP from LyondellBasell). The trisamide compounds (i.e., Compounds 1-20) were each added gravimetrically to pellets of the polymer (0.80 gram of powder additive per 1000 gm of additive/polymer mixture to obtain 800 ppm trisamide compound) and then mixed in a Henschel high intensity mixer. The resulting mixture was melt compounded on a Deltaplast single screw compounding extruder with a 25 mm screw diameter and length/diameter ratio of 30:1 at 260° C. The extrudate (in the form a strand) for each sample was cooled in a water bath and subsequently pelletized. The melt-compounded polymer composition was then injection molded using a 40-ton ARBURG ALLROUNDER 221K injection molding machine to produce plaques with dimensions of approximately 51 mm×76 mm with a thickness of 0.76 mm with a 260° C. flat profile barrel temperature and 100 bar backpressure. Plaque dimensions were verified with a micrometer after aging for 24 hours.

The percent haze of the plaques (including a control plaque made without a trisamide compound) was then measured in accordance with ASTM Standard D1103-92 using a BYK-Gardner Haze-Guard Plus.

The plaques were also tested to determine the amount of the trisamide compound that was extracted using a specified set of conditions. In particular, extractions were conducted at 100° C. for 2 hours using 550 mL stainless steel vessels with Teflon-lined, stainless steel lids. Glass spacers were used to ensure separation of polymer samples during migration testing. Extractions utilized 25% ethanol solutions. Ethanol was absolute grade. Water was deionized and obtained using an ion exchange purification system. Duplicated migration tests in solvent were performed using two plaques immersed in 250 mL of solvent. Control plaques were also prepared without a trisamide compound and extracted using the conditions described above. Aliquots (~1 mL) were removed from extraction solvents after each heating time to a vial for LC analysis.

A 1000 ppm solution of each trisamide compound was prepared by dissolving 0.100 g in NMP and dilutions were prepared in 100% Ethanol. These solutions were used to obtain a calibration plot for each trisamide compound. Water ACQUITY UPLC with Phenomenex Kinetex (particle size 2.6 µm) as analytical column and both PDA and MS as detectors were used as LC apparatus. Column temperature was 40° C. The mobile phase used was methanol and water. The flow rate was set at 0.4 mL/min. The sample injection volume was 1-5 µL. The mass spectrometer was used in single ion recording (SIR) mode using SQD2 detector. The wavelength in the PDA detector was set at 200-800 nm. Each trisamide compound was identified by comparison of its retention time with corresponding peaks in the standard solution and its MS and UV spectrum. Quantification was carried out using a calibration plot of an external standard. The limit of detection (LOD) was determined by extrapolation to a signal to noise ratio of 3:1.

The results of the haze and extraction measurements are set forth in Table 2 below. In the column for the amount extracted, the notation "N.D." means "none detected," indicating that the amount (if any) of the trisamide compound extracted could not be quantified because the measurement did not return a signal that exceeded the limit of detection (LOD) noted above.

TABLE 2

Extraction and haze measurements for polymer compositions made with Compounds 1-20 and the control polymer composition.

| Compound ID | Amount extracted (ppb) | Haze (%) |
| --- | --- | --- |
| None (Control) | — | 39.3 |
| Compound 1 | 458 | 15.1 |
| Compound 2 | 2 | 6.1 |
| Compound 3 | N.D. | 14.5 |
| Compound 4 | 4 | 3.9 |
| Compound 5 | 5 | 4.0 |
| Compound 6 | 5 | 7.5 |
| Compound 7 | N.D. | 3.6 |
| Compound 8 | 14 | 4.1 |
| Compound 9 | 15 | 16.8 |
| Compound 10 | 20 | 3.8 |
| Compound 11 | 22 | 15.3 |
| Compound 12 | 35 | 11.6 |
| Compound 13 | N.D. | 4.5 |
| Compound 14 | 49 | 5.5 |
| Compound 15 | 55 | 10.2 |
| Compound 16 | N.D. | 4.5 |
| Compound 17 | 91 | 11.6 |
| Compound 18 | 276 | 9.8 |
| Compound 19 | 303 | 17.4 |
| Compound 20 | 477 | 25.5 |

As can be seen from the data in Table 2, the polymer compositions made with trisamide compounds of Formula (I) in which $R^1$, $R^2$, and $R^3$ are each alkyl groups (i.e., polymer compositions made with Compounds 2-18) exhibited a desirable combination of low haze and extraction as compared to compositions made with trisamide compounds in which at least of $R^1$, $R^2$, and $R^3$ is a non-alkyl group (i.e., polymer compositions made with Compounds 1, 19, and 20). The difference in extraction levels is even more pronounced when the $R^1$, $R^2$, and $R^3$ groups of the trisamide compounds are alkyl groups having two or more carbon atoms (e.g., $C_3$ alkyl or longer). Further, the haze and extraction levels were consistently lower when at least one of $R^1$, $R^2$, and $R^3$ is a branched alkyl group, with the desirable performance generally being even greater with increasing numbers of branched alkyl groups.

In view of the above, the inventors believe that the trisamide compounds of the invention are exceptional due to their very desirable combination of low haze and low extraction. It is believed that polymer compositions made with such trisamide compounds will be suitable for a wide range of applications that require polymer compositions exhibiting low haze and extraction levels (e.g., food contact and medical device applications).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A compound of Formula (I)

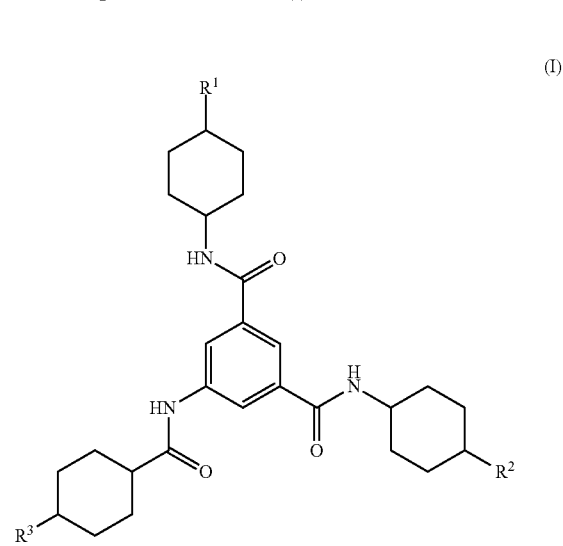

wherein $R^1$, $R^2$, and $R^3$ are independently selected from the group consisting of alkyl groups, and each of $R^1$, $R^2$, and $R^3$ is disposed in the cis-position relative to the non-hydrogen substituent attached to the 1-position of the corresponding cyclohexanediyl moiety.

2. The compound of claim 1, wherein $R^1$, $R^2$, and $R^3$ are independently selected from the group consisting of $C_1$-$C_8$ alkyl groups.

3. The compound of claim 1, wherein at least one of $R^1$, $R^2$, and $R^3$ is a branched alkyl group.

4. The compound of claim 3, wherein $R^3$ is a branched alkyl group.

5. The compound of claim 3, wherein at least two of $R^1$, $R^2$, and $R^3$ are branched alkyl groups.

6. The compound of claim 5, wherein each of $R^1$, $R^2$, and $R^3$ is a branched alkyl group.

7. The compound of claim 1, wherein the compound is selected from the group consisting of:
- N,N-di(cis-4-isopropylcyclohexyl)-5-(cis-4-n-propylcyclohexylcarbonylamino)isophthalamide;
- N,N-di(cis-4-isopropylcyclohexyl)-5-(cis-4-isopropylcyclohexylcarbonylamino)isophthalamide;
- N,N-di(cis-4-isopropylcyclohexyl)-5-(cis-4-n-butylcyclohexylcarbonylamino)isophthalamide;
- N,N-di(cis-4-isopropylcyclohexyl)-5-(cis-4-tert-butylcyclohexylcarbonylamino)isophthalamide;
- N,N-di(cis-4-isopropylcyclohexyl)-5-(cis-4-n-pentylcyclohexylcarbonylamino)isophthalamide;
- N,N-di(cis-4-isopropylcyclohexyl)-5-(cis-4-tert-pentylcyclohexylcarbonylamino)isophthalamide;
- N,N-di(cis-4-n-butylcyclohexyl)-5-(cis-4-n-butylcyclohexylcarbonylamino)isophthalamide;
- N,N-di(cis-4-n-butylcyclohexyl)-5-(cis-4-tert-butylcyclohexylcarbonylamino)isophthalamide;
- N,N-di(cis-4-sec-butylcyclohexyl)-5-(cis-4-sec-butylcyclohexylcarbonylamino)isophthalamide;
- N,N-di(cis-4-sec-butylcyclohexyl)-5-(cis-4-tert-butylcyclohexylcarbonylamino)isophthalamide;
- N,N-di(cis-4-tert-butylcyclohexyl)-5-(cis-4-n-propylcyclohexylcarbonylamino)isophthalamide;
- N,N-di(cis-4-tert-butylcyclohexyl)-5-(cis-4-isopropylcyclohexylcarbonylamino)isophthalamide;
- N,N-di(cis-4-tert-butylcyclohexyl)-5-(cis-4-n-butylcyclohexylcarbonylamino)isophthalamide;
- N,N-di(cis-4-tert-butylcyclohexyl)-5-(cis-4-tert-butylcyclohexylcarbonylamino)isophthalamide;
- N,N-di(cis-4-tert-butylcyclohexyl)-5-(cis-4-n-pentylcyclohexylcarbonylamino)isophthalamide;
- N,N-di(cis-4-tert-pentylcyclohexyl)-5-(cis-4-tert-butylcyclohexylcarbonylamino)isophthalamide;
- N,N-di(cis-4-tert-pentylcyclohexyl)-5-(cis-4-tert-pentylcyclohexylcarbonylamino)isophthalamide;
- and mixtures thereof.

8. The compound of claim 7, wherein the compound is N,N-di(cis-4-tert-butylcyclohexyl)-5-(cis-4-tert-butylcyclohexylcarbonylamino)isophthalamide.

9. The compound of claim 7, wherein the compound is N,N-di(cis-4-tert-butylcyclohexyl)-5-(cis-4-isopropylcyclohexylcarbonylamino)isophthalamide.

10. The compound of claim 7, wherein the compound is N,N-di(cis-4-tert-butylcyclohexyl)-5-(cis-4-n-butylcyclohexylcarbonylamino)isophthalamide.

11. The compound of claim 7, wherein the compound is N,N-di(cis-4-tert-pentylcyclohexyl)-5-(cis-4-tert-butylcyclohexylcarbonylamino)isophthalamide.

12. The compound of claim 7, wherein the compound is N,N-di(cis-4-tert-butylcyclohexyl)-5-(cis-4-n-propylcyclohexylcarbonylamino)isophthalamide.

13. The compound of claim 7, wherein the compound is N,N-di(cis-4-isopropylcyclohexyl)-5-(cis-4-tert-butylcyclohexylcarbonylamino)isophthalamide.

14. The compound of claim 7, wherein the compound is N,N-di(cis-4-tert-pentylcyclohexyl)-5-(cis-4-tert-pentylcyclohexylcarbonylamino)isophthalamide.

15. The compound of claim 7, wherein the compound is N,N-di(cis-4-isopropylcyclohexyl)-5-(cis-4-n-butylcyclohexylcarbonylamino)isophthalamide.

16. The compound of claim 7, wherein the compound is N,N-di(cis-4-isopropylcyclohexyl)-5-(cis-4-n-pentylcyclohexylcarbonylamino)isophthalamide.

17. The compound of claim 7, wherein the compound is N,N-di(cis-4-tert-butylcyclohexyl)-5-(cis-4-n-pentylcyclohexylcarbonylamino)isophthalamide.

18. The compound of claim 7, wherein the compound is N,N-di(cis-4-isopropylcyclohexyl)-5-(cis-4-tert-pentylcyclohexylcarbonylamino)isophthalamide.

19. The compound of claim 7, wherein the compound is N,N-di(cis-4-isopropylcyclohexyl)-5-(cis-4-n-propylcyclohexylcarbonylamino)isophthalamide.

20. The compound of claim 7, wherein the compound is N,N-di(cis-4-n-butylcyclohexyl)-5-(cis-4-tert-butylcyclohexylcarbonylamino)isophthalamide.

21. The compound of claim 7, wherein the compound is N,N-di(cis-4-n-butylcyclohexyl)-5-(cis-4-n-butylcyclohexylcarbonylamino)isophthalamide.

22. The compound of claim 7, wherein the compound is N,N-di(cis-4-sec-butylcyclohexyl)-5-(cis-4-sec-butylcyclohexylcarbonylamino)isophthalamide.

23. The compound of claim 7, wherein the compound is N,N-di(cis-4-sec-butylcyclohexyl)-5-(cis-4-tert-butylcyclohexylcarbonylamino)isophthalamide.

24. A polymer composition comprising:
(a) a compound of claim 1; and
(b) a polyolefin polymer.

25. The polymer composition of claim 24, wherein the polyolefin polymer is a polypropylene polymer.

26. The polymer composition of claim 25, wherein the polyolefin polymer is selected from the group consisting of polypropylene homopolymers, polypropylene random copolymers, and mixtures thereof.

27. The polymer composition of claim 26, wherein the polyolefin polymer is a polypropylene random copolymer.

28. The polymer composition of claim 24, wherein the compound of Formula (I) is present in the composition in an amount of about 0.001 wt. % or more, based on the total weight of the polymer composition.

* * * * *